United States Patent [19]
Stracheljahn

[11] Patent Number: 5,811,642
[45] Date of Patent: Sep. 22, 1998

[54] PUMPKIN VARIETY RS1294

[75] Inventor: Robert Stracheljahn, St. Jacob, Ill.

[73] Assignee: Rupp Seeds Inc., Wauseon, Ohio

[21] Appl. No.: 741,766

[22] Filed: Nov. 5, 1996

[51] Int. Cl.⁶ .............................. A01H 5/10; A01H 5/00; A01H 1/04; C12N 5/04

[52] U.S. Cl. .................... 800/200; 800/250; 800/255; 800/DIG. 20; 47/58; 47/DIG. 1; 435/410

[58] Field of Search ...................... 800/200, 250, 800/255, DIG. 20; Plt./33.1, 54.1; 47/58, DIG. 1; 435/419

[56] References Cited

PUBLICATIONS

Precheur. Pumpkin Variety Update. Vegetable Research News. Ohio State University, Dec. 1995.

*Primary Examiner*—David T. Fox
*Assistant Examiner*—Melissa L. Kimball
*Attorney, Agent, or Firm*—Rothwell, Figg, Ernst & Kurz

[57] ABSTRACT

A novel pumpkin variety, designated RS1294, is disclosed. The invention relates to the seeds of pumpkin variety RS1294, to the plants of pumpkin variety RS1294 and to methods for producing a pumpkin plant produced by crossing the variety RS1294 with itself or another pumpkin line. The invention further relates to hybrid pumpkin seeds and plants produced by crossing the variety RS1294 with another pumpkin line.

11 Claims, No Drawings

PUMPKIN VARIETY RS1294

BACKGROUND OF THE INVENTION

The present invention relates to a new and distinctive pumpkin variety, designated RS1294. It is anticipated that the pumpkin plant 'RS1294' will be domestically marketed under the synonym 'Gold Rush'. There are numerous steps in the development of any novel, desirable plant germplasm. Plant breeding begins with the analysis and definition of problems and weaknesses of the current germplasm, the establishment of program goals, and the definition of specific breeding objectives. The next step is selection of germplasm that possess the traits to meet the program goals. The goal is to combine in a single variety or hybrid an improved combination of desirable traits from the parental germplasm. These important traits may include higher yield, resistance to diseases and insects, tolerance to drought and heat, and better quality.

Choice of breeding or selection methods depends on the mode of plant reproduction, the heritability of the trait(s) being improved, and the type of cultivar used commercially (e.g., $F_1$ hybrid, variety, etc.). For highly heritable traits, a choice of superior individual plants evaluated at a single location may be effective, whereas for traits with low heritability, selection should be based on mean values obtained from replicated evaluations of families of related plants. Popular selection methods commonly include pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach has been used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

Each breeding program should include a periodic, objective evaluation of the efficiency of the breeding procedure. Evaluation criteria vary depending on the goal and objectives, but should include gain from selection per year based on comparisons to an appropriate standard, overall value of the advanced breeding lines, and number of successful cultivars produced per unit of input (e.g., per year, per dollar expended, etc.).

Promising advanced breeding lines are thoroughly tested and compared to appropriate standards in environments representative of the commercial target area(s). The best lines are candidates for new commercial cultivars; those still deficient in a few traits are used as parents to produce new populations for further selection.

These processes, which lead to the final step of marketing and distribution, usually take from ten to 30 years from the time the first cross is made. Therefore, development of new cultivars is a time-consuming process that requires precise forward planning, efficient use of resources, and a minimum of changes in direction.

A most difficult task is the identification of individuals that are genetically superior, because for most traits the true genotypic value is masked by other confounding plant traits or environmental factors. One method of identifying a superior plant is to observe its performance relative to other experimental plants and to a widely grown standard cultivar. If a single observation is inconclusive, replicated observations provide a better estimate of its genetic worth.

The goal of plant breeding is to develop new, unique and superior pumpkin varieties and hybrids. The breeder initially selects and crosses two or more parental lines, followed by repeated selection, producing many new genetic combinations. The breeder can theoretically generate billions of different genetic combinations via crossing, selfing and mutations. The breeder has no direct control at the cellular level. Therefore, two breeders will never develop the same line, or even very similar lines, having the same corn traits.

Each year, the plant breeder selects the germplasm to advance to the next generation. This germplasm is grown under unique and different geographical, climatic and soil conditions, and further selections are then made, during and at the end of the growing season. The varieties which are developed are unpredictable. This unpredictability is because the breeder's selection occurs in unique environments, with no control at the DNA level (using conventional breeding procedures), and with millions of different possible genetic combinations being generated. A breeder of ordinary skill in the art cannot predict the final resulting lines he develops, except possibly in a very gross and general fashion. The same breeder cannot produce the same variety twice by using the exact same original parents and the same selection techniques. This unpredictability results in the expenditure of large research monies to develop superior new pumpkin varieties.

The development of commercial pumpkin hybrids requires the development of varieties, the crossing of these varieties, and the evaluation of the crosses. Pedigree breeding and recurrent selection breeding methods are used to develop varieties from breeding populations. Breeding programs combine desirable traits from two or more varieties or various broad-based sources into breeding pools from which varieties are developed by crossing and selection of desired phenotypes. The new varieties are crossed with other varieties and the hybrids from these crosses are evaluated to determine which have commercial potential.

Pedigree breeding is used commonly for the improvement of both self-pollinating and cross-pollinating crops. Two parents which possess favorable, complementary traits are crossed to produce an $F_1$. An $F_2$ population is produced by selfing one or several $F_1$'s or by intercrossing two $F_1$'s (sib mating). Selection of the best individuals is usually begun in the $F_2$ population; then, beginning in the $F_3$, the best individuals in the best families are selected. At an advanced stage of inbreeding (i.e., $F_6$ and $F_7$), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or inbred line which is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

Descriptions of other breeding methods that are commonly used for different traits and crops can be found in one of several reference books (e.g., Allard, 1960; Simmonds, 1979; Sneep et al., 1979; Fehr, 1987, Basset, 1986).

Proper testing should detect any major faults and establish the level of superiority or improvement over current cultivars. In addition to showing superior performance, there must be a demand for a new cultivar that is compatible with industry standards or which creates a new market. The introduction of a new cultivar will incur additional costs to the seed producer, the grower, processor and consumer; for special advertising and marketing, altered seed and commercial production practices, and new product utilization. The testing preceding release of a new cultivar should take into consideration research and development costs as well as technical superiority of the final cultivar. For seed-propagated cultivars, it must be feasible to produce seed easily and economically.

Once the varieties that give the best hybrid performance have been identified, the hybrid seed can be reproduced indefinitely as long as the homogeneity of the parent is maintained. A single-cross hybrid is produced when two varieties are crossed to produce the $F_1$ progeny. A double-cross hybrid is produced from four varieties crossed in pairs (A×B and C×D) and then the two $F_1$ hybrids are crossed again (A×B)×(C×D). Much of the hybrid vigor exhibited by $F_1$ hybrids is lost in the next generation ($F_2$).

Pumpkin is an important and valuable crop. Thus, a continuing goal of plant breeders is to develop stable, high yielding pumpkins that are agronomically sound. The reasons for this goal are obviously to maximize the total yield and quality produced on the land used. To accomplish this goal, the pumpkin breeder must select and develop pumpkin plants that have the traits that result in superior varieties and hybrids.

SUMMARY OF THE INVENTION

According to the invention, there is provided a novel pumpkin variety, designated RS1294. This invention thus relates to the seeds of pumpkin variety RS1294, to the plants of pumpkin variety RS1294 and to methods for producing a pumpkin plant produced by crossing the variety RS1294 with itself or another pumpkin variety. This invention further relates to hybrid pumpkin seeds and plants produced by crossing the variety RS1294 with another pumpkin variety.

DEFINITIONS

In the description and tables which follow, a number of terms are used. In order to provide a clear and consistent understanding of the specification and claims, including the scope to be given such terms, the following definitions are provided:

Fruit—The total number of fruit harvested for a specific size category.

Average Fruit Wt.—The average weight in pounds of pumpkin fruit.

Total Wt.—The total weight in pounds of all fruit for a given size category.

Adjusted Yield per Acre—Total yield of pumpkin fruits in pounds adjusted to a per acre basis.

DETAILED DESCRIPTION OF THE INVENTION

Pumpkin variety RS1294 is a winter pumpkin of the species *pepo* with superior characteristics. Pumpkin variety RS1294 was developed by mass selection from the variety Connecticut Field and selected for thick stems. These selections were then crossed with a large gourd of unknown origin and then further selected using mass selection. Bees randomly cross pollinated these new varieties with the mass selected lines. The best fruit were selected and harvested and seed from these selected fruit were used for planting and for further selection the following year. RS1294 plants and fruits have been selected for uniformity and have been found to breed true to type and are as uniform as other pumpkin varieties of its class.

VARIETY DESCRIPTION INFORMATION

Winter Pumpkin
Genus: Cucurbita
Species: *pepo*
A. Cotyledon:
    Length (mm): 85
    Width (mm): 45
    Apex: Rounded
    Veining: Plainly visible
    Color: Medium Green
B. Plant: Long vines prickly
C. Main Stem: Angled
    Average length (cm): 530
    Diameter at midpoint of first internode (mm): 32
    Average number of internodes: 70
D. Leaves:
    Shape: Reniform; deep lobed
    Margin: Denticulate, flat
    Width (cm): 45
    Length (cm): 35
    Surface: smooth
    Dorsal surface: bristled
    Ventral surface: bristled
    Color: Medium green, not blotched
    Petiole length (cm): 35
E. Flower—Pistillate
    Diameter (cm): 17
    Ovary: Fusiform
    Pedicel length (cm): 2
    Margin: curved, plain
    Sepals width (mm): 55 Length (mm): 10
    Color: deep yellow
F. Flower—staminate:
    Sepals: width (mm): 70 Length (mm): 95
    Pedicil length (cm): 20
    Color: deep yellow
G. Fruit:
    Length (cm): 36
    Width (cm) stem end: 28
    Width (cm) blossom end: 30
    Average weight (gm): 11,300
    Shape according to variety type: Connecticut Field
    Apex: depressed
    Base: depressed
    Ribs: prominant
    Rib furrows: shallow, narrow
    Fruit surface: shallowly wavy
    Warts: none
    Blossom scar button: depressed H. Rind:
  Thickness at medial (mm): 2
  Rind: hard
  Color pattern: regular, grayish-buff
I. Flesh:
  Thickness: Blossom end (mm): 40
  Medial (mm): 50
  Stem end (mm): 45
  Texture: granular, brittle, moist
  Flavor: slightly sweet
  Quality: good
  Color: yellow-orange
J. Seed Cavity (sectioned apex to base)
  Length (cm): 19
  Width (cm): 24
  Location: conforms to fruit shape
  Placental Tissue: moderately abundant
  Center core: inconspicuous
K. Fruit Stalks: irregular, twisted, tapered, slightly curved
  Length (cm): 20
  Diameter (cm): 9
  Texture: hard
  Farrows: deep
  Surface: spiny
  Attachment end: expanded
  Detaches: with difficulty
  Color: dark green
L. Seeds
  Length (mm): 19
  Width (mm): 10
  Thickness (mm): 3
  Face Surface: smooth
  Color: cream
  Luster: glossy
  Margin: curved, rounded
  Separation from pulp: moderately easy
  Grams per 100 seeds: 17
  No. seeds per fruit: 550

This invention is also directed to methods for producing a pumpkin variety by crossing a first parent pumpkin variety with a second parent pumpkin variety, wherein the first or second pumpkin variety is the pumpkin plant from the variety RS1294. Further, both first and second parent pumpkin plants may be from the variety RS1294. Therefore, any methods using the pumpkin variety RS1294 are part of this invention; including selfing, backcrosses, hybrid breeding, and crosses to populations. Any plants produced using pumpkin variety RS1294 as a parent are within the scope of this invention. Advantageously, the pumpkin variety is used in crosses with other pumpkin varieties to produce first generation ($F_1$) hybrid seed and plants with superior characteristics.

As used herein, the term "plant" includes plant cells, plant protoplasts, plant cell of tissue culture from which pumpkin plants can be regenerated, plant calli, plant clumps, and plant cells that are intact in plants or parts of plants, such as pollen, flowers, kernels, ears, cobs, leaves, husks, stalks, and the like.

The closest prior variety to RS1294 is the pumpkin variety Connecticut Field.

RS1294 is a "medium maturation date" of approximately 110–120 growing days. The most unique character of RS1294 is the greatly enlarged stem, which is hard and angular. The basal attachment ranges from 8 to 14 cm across. The angular ridges of the stem flare out into the flesh, creating distinct raised ridges 10 to 20 cm long, across the top and down the sides of the pumpkin. This unique attachment is very strong and resists breakage or snapping off at the base during handling. This stem structure was acquired through crossing with gourd type C. pepo during variety development.

The rind or outer shell texture of RS1294 is exceptionally hard and resists scratching and scaring during handling. RS1294 has a consistently thick flesh (40–50 mm) which resists crushing and bruising, and fruit shape, firmness and integrity is maintained during the rigors of bulk packing and transport. The flesh of RS1294 is very granular with high moisture levels. Weight to size ratio is high. The seed set in RS1294 is moderate, with a range of 500–600 seeds per fruit and the seeds range in weight from 13–21 grams/100 sseeds. For pumpkin preparation purposes, seeds and placenta are very compact, "clean", and easily removed.

TABLES

In the tables that follow, the traits and characteristics of pumpkin variety RS1294 are presented. The data collected on pumpkin variety RS1294 is presented for the key characteristics and traits. Information about RS1294, as compared to several check varieties, is presented.

In Table 1 RS1294 is compared to other pumpkin varieties at a variety trial conducted at the University of Tennessee. In Table 2, RS1294 is comparaed to other pumpkin varieties at Oregon, Ohio. Information for the different varieties includes:

1. Variety Name—which is the name given various pumpkin varieties in the industry.

2. Number of Pumpkins—Number of Pumpkins grown in a particular plot.

3. Total Weight—Total weight (Total Wt.) of all fruit in that variety's particular plot.

4. Tons per Acre—Weight of pumpkin fruit calculated per acre.

5. Average Fruit Weight—An average weight in pounds of the number of pumpkins grown in that variety's particular plot.

6. Number Discarded—This was determined by immature or poorly shaped fruit that is not marketable.

7. Number Immature—This was determined by immature green fruit.

TABLE 1

1996 Pumpkin Variety Trial
University of Tennessee, Bledsoe County

| Variety | No. of Pumpkins | Total Weight | Average Weight | No. Discarded | No. Immature |
| --- | --- | --- | --- | --- | --- |
| Pro Gold #300 | 36 | 580 | 16.1 | 7 | 1 |
| RS1090 Jumpin Jack ® | 27 | 590 | 21.9 | 3 | 2 |
| Rogers 90s523 | 42 | 965 | 22.9 | 6 | 1 |
| Peek-a-Boo | 86 | 325 | 3.8 | 0 | 0 |
| ProGold #510 | 29 | 925 | 31.9 | 10 | 5 |
| Aspen | 55 | 975 | 17.7 | 3 | 2 |
| Jack of all Trades | 42 | 630 | 15.0 | 2 | 6 |
| ProGold #520 | 26 | 600 | 23.1 | 3 | 1 |
| Fat Boy | 22 | 350 | 15.9 | 2 | 5 |
| Gold Rush | 13 | 375 | 28.8 | 1 | 0 |
| RS1294 | | | | | |
| Oz | 73 | 235 | 3.2 | 0 | 0 |
| Rogers 92p159 | 31 | 340 | 10.9 | 2 | 5 |
| Spookie | 82 | 255 | 3.1 | 0 | 0 |
| Appalachian | 34 | 545 | 16.0 | 0 | 5 |
| Rupp 94P497 | 10 | 115 | 11.5 | 0 | 0 |

TABLE 1-continued

1996 Pumpkin Variety Trial
University of Tennessee, Bledsoe County

| Variety | No. of Pumpkins | Total Weight | Average Weight | No. Discarded | No. Immature |
|---|---|---|---|---|---|
| Howden | 25 | 480 | 19.2 | 2 | 2 |
| Ichabod | 22 | 425 | 19.3 | 0 | 3 |
| Appalachian | 42 | 680 | 16.2 | 1 | 8 |
| Rupp 3PH20 | 41 | 825 | 20.1 | 0 | 0 |
| Rupp 3PH18 | 37 | 750 | 20.3 | 1 | 0 |
| Mother Lode F1 | 32 | 625 | 19.5 | 3 | 3 |
| Rupp 94p502 | 11 | 185 | 16.8 | 0 | 3 |
| Gold Strike F1 Rupp 94p510 | 13 | 310 | 23.8 | 4 | 1 |
| Rupp 3PH25 | 27 | 395 | 14.6 | 4 | 0 |

TABLE 2

1996 PUMPKIN VARIETY TRIAL
Clay High School, Oregon, Ohio

| Variety | No. of Pumpkins | Total Weight | Tons per Acre | Average Weight | Largest Fruit |
|---|---|---|---|---|---|
| Mother Lode HSR-896 | 42 | 801 | 17.45 | 19.07 | 39 |
| Jack B Little | | 170 | 3.70 | | |
| Ichabod | 31 | 547 | 11.91 | 17.65 | 31 |
| Autumn Gold | 77 | 602 | 13.11 | 9.45 | 11 |
| Rupp 3-PH-20 | 44 | 1065 | 23.20 | 21.2 | 38 |
| Big Autumn | 65 | 614 | 13.37 | 9.45 | 15 |
| Rupp 94-P-497 | 40 | 712 | 15.51 | 17.8 | 28 |
| Prizewinner | 16 | 1111 | 24.2 | 69.44 | 104 |
| Rupp 3-PH-25 | 68 | 987 | 21.5 | 14.51 | 30 |
| Peek-a-Boo | 75 | 222 | 4.84 | 2.96 | 4 |
| Jumpin Jack ® | 56 | 1077 | 23.46 | 19.23 | 38 |
| Jack B Quik | 75 | | 1.63 | | |
| Howden | 17 | 315 | 6.86 | 18.53 | 34 |
| Baby Pam | 72 | 157 | 3.42 | 2.18 | 3.5 |
| Baby Bear | 147 | 167 | 3.64 | 1.14 | 2 |
| Prizzewinner | 15 | 1276 | 27.79 | 85.06 | 184 |
| Funny Face | 73 | 822 | 17.9 | 11.26 | 18 |
| Oz | 182 | 545 | 11.87 | 2.99 | 4 |
| Rocket | 57 | 629 | 13.7 | 11.04 | 17.5 |
| Prizewinner | 16 | 1103 | 24.02 | 68.94 | 111 |
| Harvest Moon | 53 | 560 | 12.22 | 10.57 | 15 |
| Sugar Treat | 124 | 425 | 9.26 | 3.40 | 4.05 |
| Jumpin Jack ® | 71 | 1376 | 29.97 | 19.38 | 47 |
| Sm Sugar (Asgrow) | 128 | 422 | 9.19 | 3.30 | 6 |
| Thomas Halloween | 41 | 683 | 16.66 | 16.67 | 23 |
| Spookie | 139 | 502 | 10.93 | 3.61 | 5.5 |
| Rupp 3-PH-18 | 37 | 768 | 16.73 | 20.76 | 23 |
| Triple Treat | 82 | 353 | 7.69 | 4.30 | 7.5 |
| Gold Strike 94p510 | 36 | 623 | 13.57 | 17.31 | 30 |
| Prizewinner | 17 | 1557 | 33.91 | 91.59 | 160 |
| Frosty | 82 | 793 | 17.27 | 9.67 | 18 |
| Baby Boo | | 175 | 3.81 | | |
| Jumpin Jack ® | 44 | 881 | 19.19 | 20.02 | 40 |
| Jack B Quik | | 50 | 1.09 | | |
| Howden Biggie | 33 | 748 | 16.29 | 22.67 | 34 |
| Tom Fox | 56 | 534 | 11.63 | 10.96 | 20 |
| Jack of All Trades | 56 | 534 | 11.63 | 9.54 | 18.5 |
| Casper | 40 | 344 | 7.49 | 8.60 | 14 |
| Connecticut field | 36 | 540 | 11.76 | 15.0 | 25 |
| Rouge | 47 | 920 | 20.04 | 19.57 | 38 |
| Trickster | 83 | 162 | 3.53 | 1.95 | 3 |
| Mixed Gourds | | 310 | 6.75 | | |
| Jackpot | 42 | 710 | 15.46 | 16.90 | 27 |
| Jack-O-Lantern | 47 | 450 | 9.80 | 9.57 | 21 |
| Ghostrider | 52 | 445 | 9.69 | 8.56 | 15 |
| Tom Fox | 45 | 440 | 9.58 | 9.78 | 18.5 |
| Gold Rush RS1294 | 36 | 808 | 17.60 | 21.84 | 46 |
| Lumina | 41 | 286 | 6.23 | 6.98 | 13 |
| Spirit | 35 | 217 | 4.73 | 6.20 | 15 |
| Pankow's Field | 53 | 543 | 11.83 | 10.25 | 16 |
| Mammoth Gold | 38 | 485 | 10.56 | 12.76 | 33 |

DEPOSIT INFORMATION

Variety seeds of RS1294 have been placed on deposit with the American Type Culture Collection (ATCC), Rockville, Md. 20852, under Deposit Accession Number 97816 on Dec. 6, 1996. A Plant Variety Protection Certificate is being applied for with the United States Department of Agriculture.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A pumpkin seed designated RS1294 having ATCC designation number 97816.

2. A plant or plants of the pumpkin variety designated RS1294 produced by growing the seed of claim 1.

3. Pollen of the variety of claim 2.

4. Ovule or ovules of the variety of claim 2.

5. A pumpkin plant with all the physiological and morphological characteristics of the pumpkin plant of claim 2.

6. The pumpkin seed of claim 1, as deposited in ATCC Deposit No. 97816.

7. Tissue culture of the plant of claim 2.

8. A pumpkin plant regenerated from the tissue culture of claim 7 having all the morphological and physiological characteristics of RS1294.

9. A method to produce a hybrid pumpkin seed comprising the steps of:

a) planting in pollinating proximity seeds of pumpkin variety RS1294 having ATCC designation number 97816 and other pumpkin variety;

b) cultivating pumpkin plants resulting from said seeds until said plants bear flowers;

c) emasculating the male flowers of the plants of either pumpkin variety;

d) allowing cross pollination to occur between said pumpkin variety; and, e) harvesting seeds produced on said emasculated plants of the pumpkin variety.

10. A first generation ($F_1$) hybrid pumpkin plant produced by growing said hybrid pumpkin seed of claim 9.

11. Seed derived from the hybrid pumpkin plant of claim 10.

* * * * *